(12) United States Patent
Han et al.

(10) Patent No.: US 8,196,471 B2
(45) Date of Patent: Jun. 12, 2012

(54) ULTRASONIC PROBE FOR PRODUCING FOUR DIMENSIONAL IMAGE

(75) Inventors: Jin Ho Han, Daegu (KR); Dong Hyun Kim, Gyeongju-si (KR); In Seong Song, Daegu (KR)

(73) Assignee: Prosonic Co., Ltd., Gyeongju-Si (KR)

( * ) Notice: Subject to any disclaimer, the term of this patent is extended or adjusted under 35 U.S.C. 154(b) by 1282 days.

(21) Appl. No.: 11/909,293

(22) PCT Filed: Mar. 24, 2006

(86) PCT No.: PCT/KR2006/001092
§ 371 (c)(1),
(2), (4) Date: Oct. 8, 2007

(87) PCT Pub. No.: WO2006/101373
PCT Pub. Date: Sep. 28, 2006

(65) Prior Publication Data
US 2010/0156404 A1    Jun. 24, 2010

(30) Foreign Application Priority Data

Mar. 24, 2005 (KR) .................. 10-2005-0024583

(51) Int. Cl.
*G01N 29/00* (2006.01)
*A61B 8/14* (2006.01)
(52) U.S. Cl. ............. 73/620; 73/623; 600/459; 600/445
(58) Field of Classification Search .............. None
See application file for complete search history.

(56) References Cited

U.S. PATENT DOCUMENTS

| | | | |
|---|---|---|---|
| 4,215,585 A | 8/1980 | Kunii | |
| 4,282,879 A * | 8/1981 | Kunii et al. | 600/445 |
| 4,541,434 A | 9/1985 | Okado | |
| 4,785,819 A * | 11/1988 | Pearce | 600/446 |
| 4,913,155 A * | 4/1990 | Dow et al. | 600/446 |
| 5,090,414 A | 2/1992 | Takano | |
| 5,361,768 A * | 11/1994 | Webler et al. | 600/445 |
| 5,417,219 A * | 5/1995 | Takamizawa et al. | 600/472 |
| 2004/0158154 A1 | 8/2004 | Hanafy | |

FOREIGN PATENT DOCUMENTS

| | | |
|---|---|---|
| EP | 1 208 800 | 5/2002 |
| KR | 10-2004-0054533 | 10/2004 |

* cited by examiner

*Primary Examiner* — Vinh Nguyen
(74) *Attorney, Agent, or Firm* — Maschoff Gilmore & Israelsen

(57) ABSTRACT

The present invention relates to an ultrasonic probe for producing a real-time three dimensional live action image (a four dimensional image), which has a long lifetime, and an improved image quality, can prevent malfunction. The ultrasonic probe for producing a four dimensional image includes power transmission means for transmission of power from an upright motor to a module (2) having acoustic elements for swinging the module, the power transmission means includes a first link (20) having a horizontal portion (22) directly connected to a motor shaft, and a sloped portion projected upward from one side end of the horizontal portion at an angle in conformity with a locus of a swing action of the module, and a second link (21) comprising a horizontal (29) having an interlocking connected thereto and a pair of parallel portion (30) and (31) projected upwardly from opposite ends of the horizontal portion, such that the second link is interlocked along the first link in a state of being interposed between the first link and the module, wherein the interlocking shaft (28) is connected with an inclined portion of the first link by a shaft and the pair of parallel portions is mounting to a lower side of the module in a horizontal direction with a shaft.

9 Claims, 7 Drawing Sheets

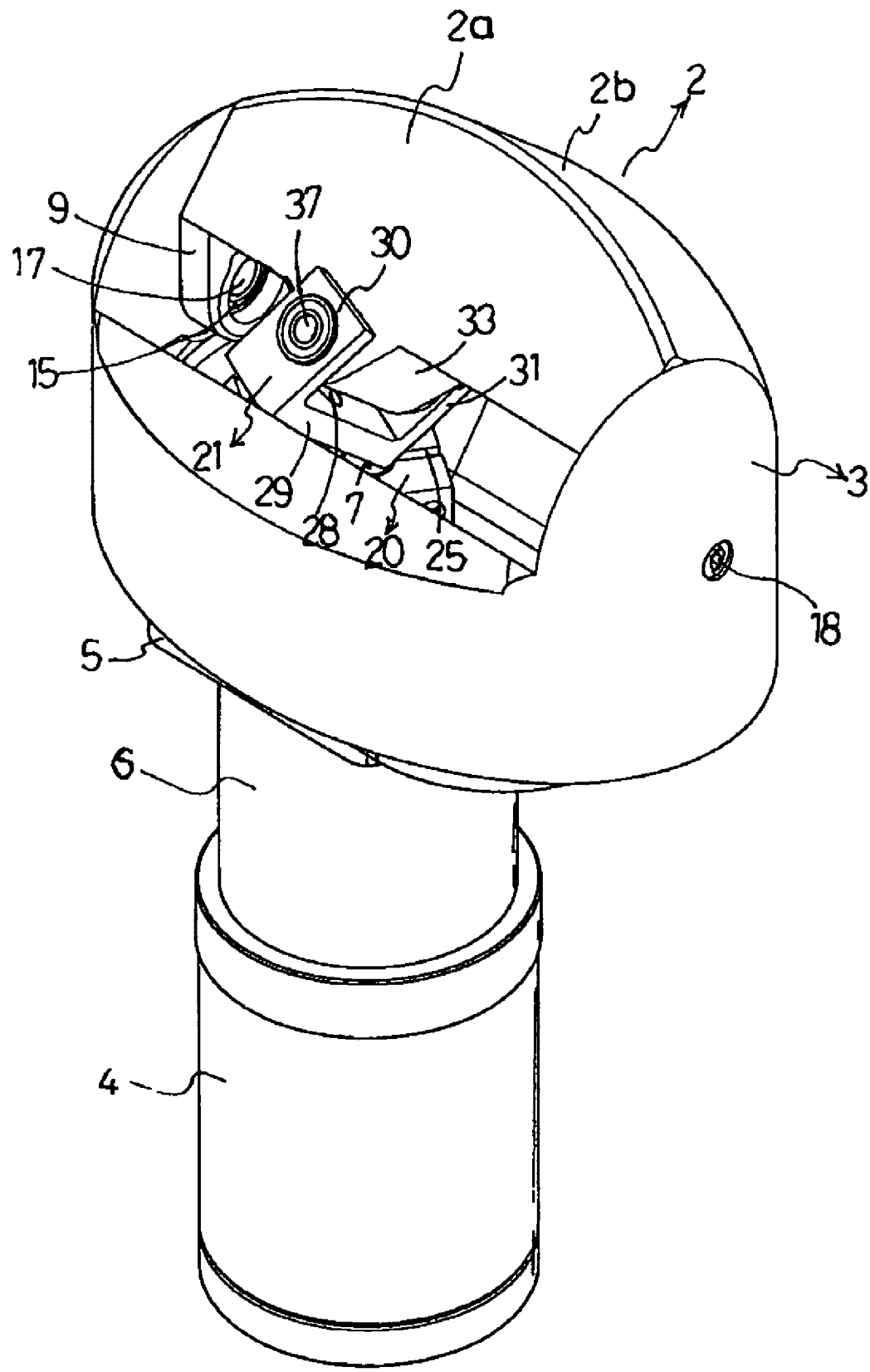
[Fig. 1]

[Fig. 2]
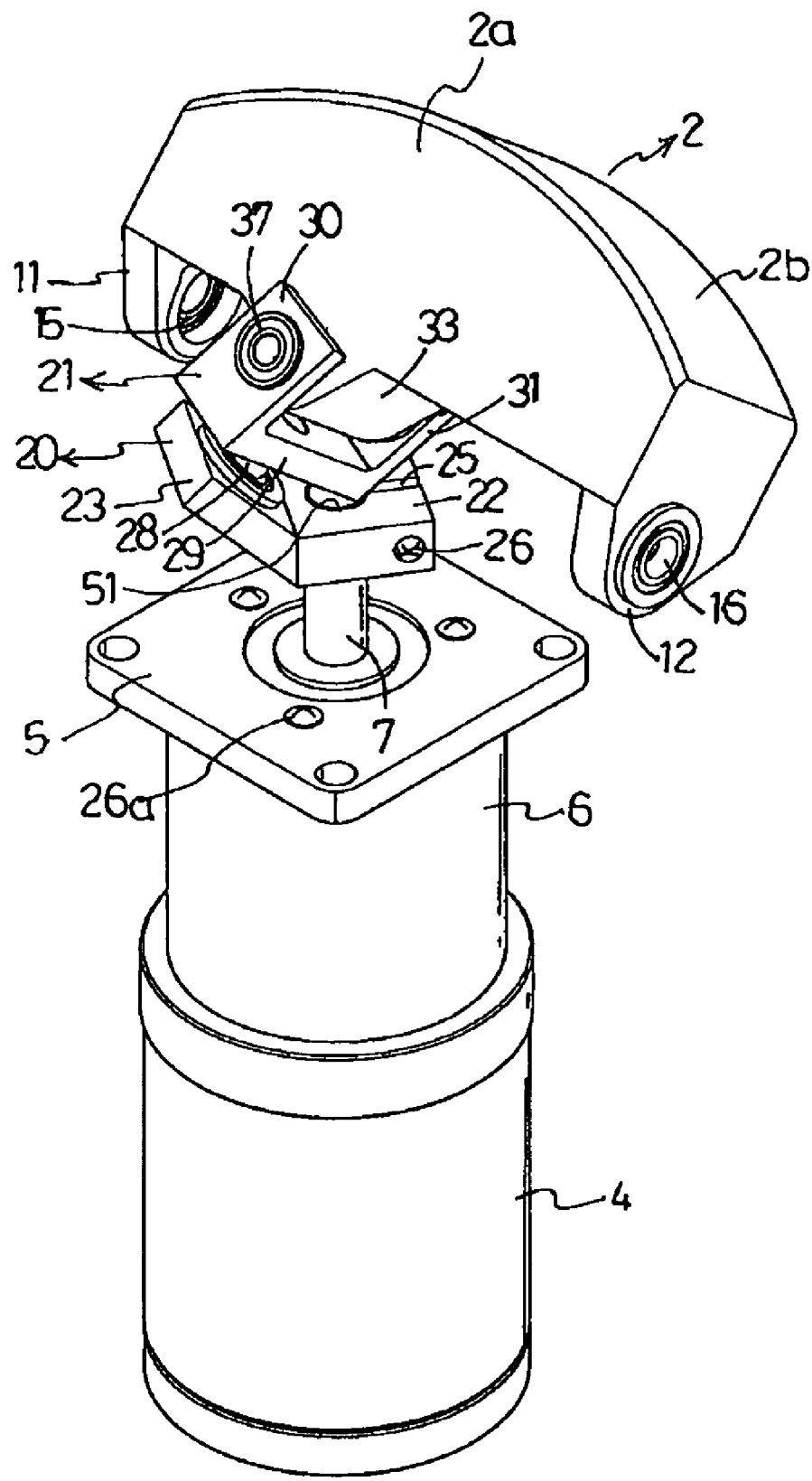

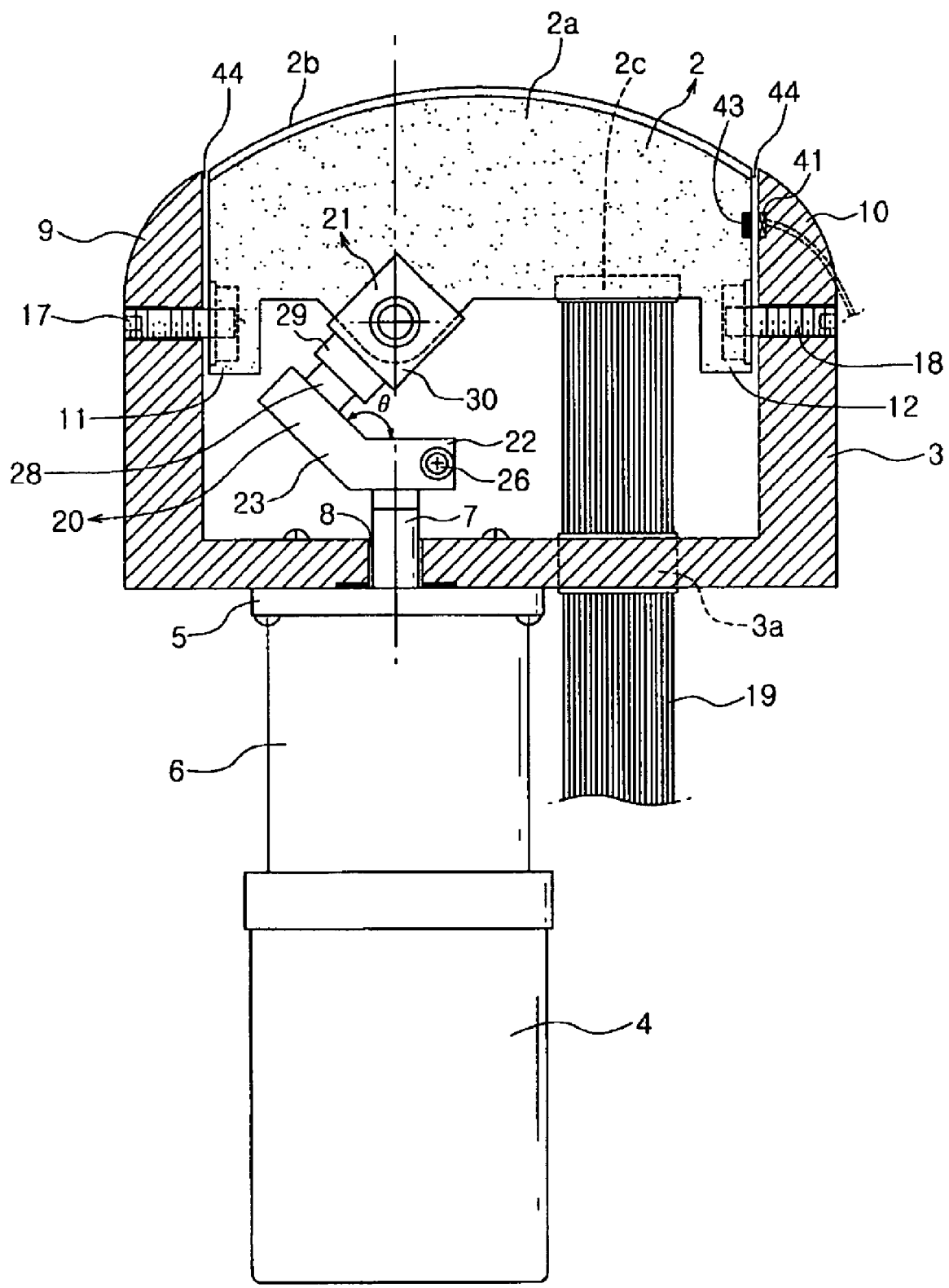
[Fig. 3]

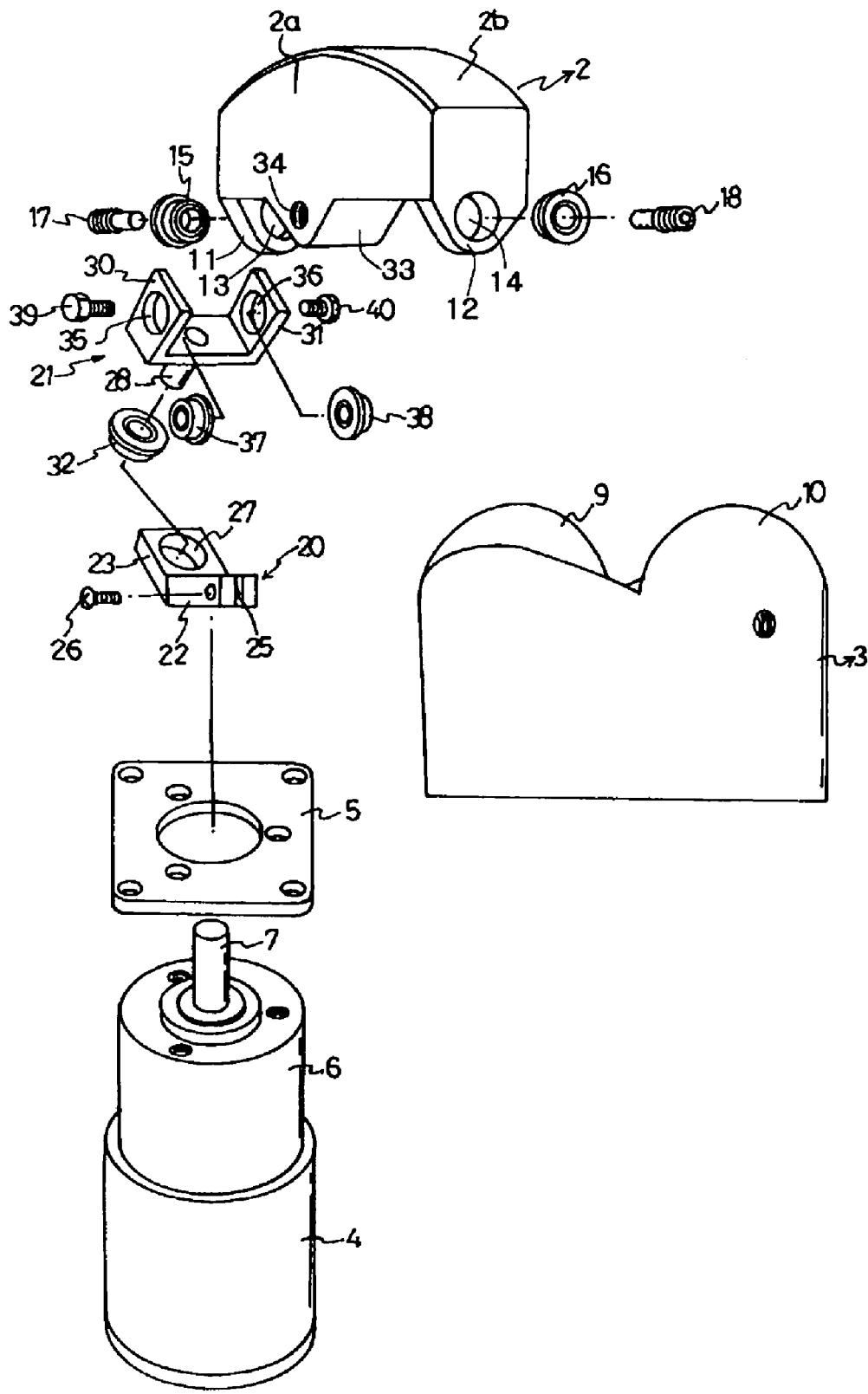
[Fig. 4]

[Fig. 5]
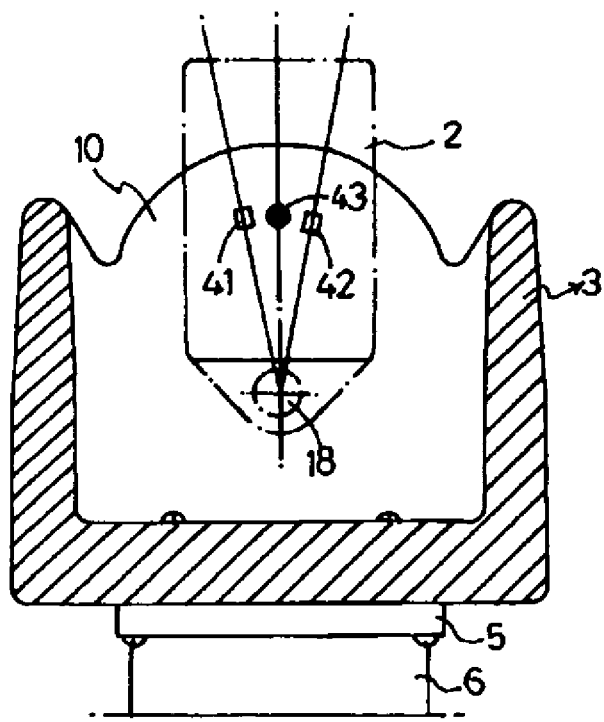
[Fig. 6]
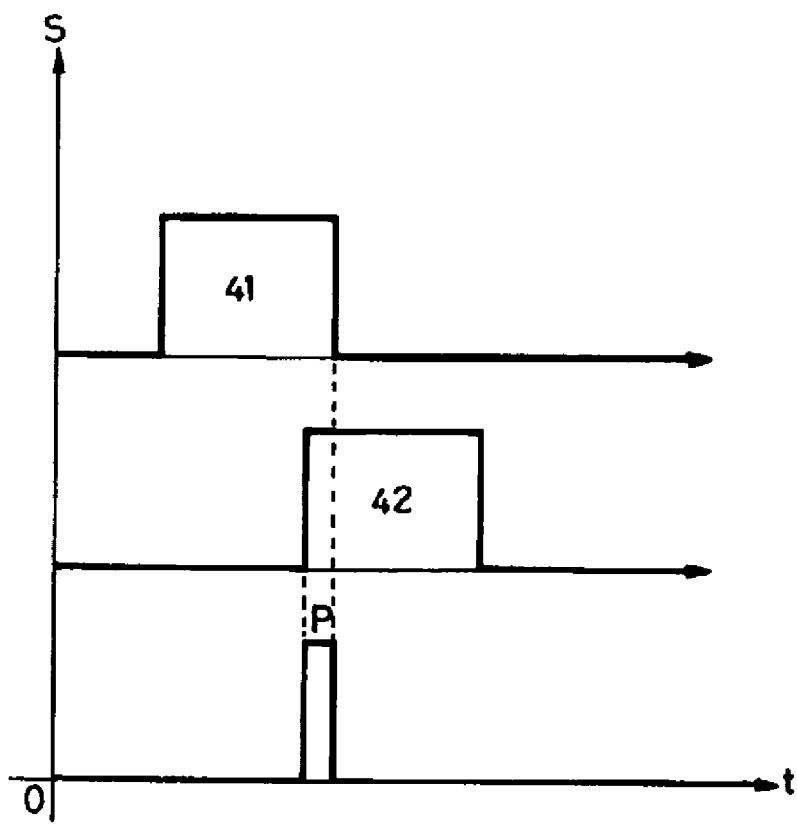

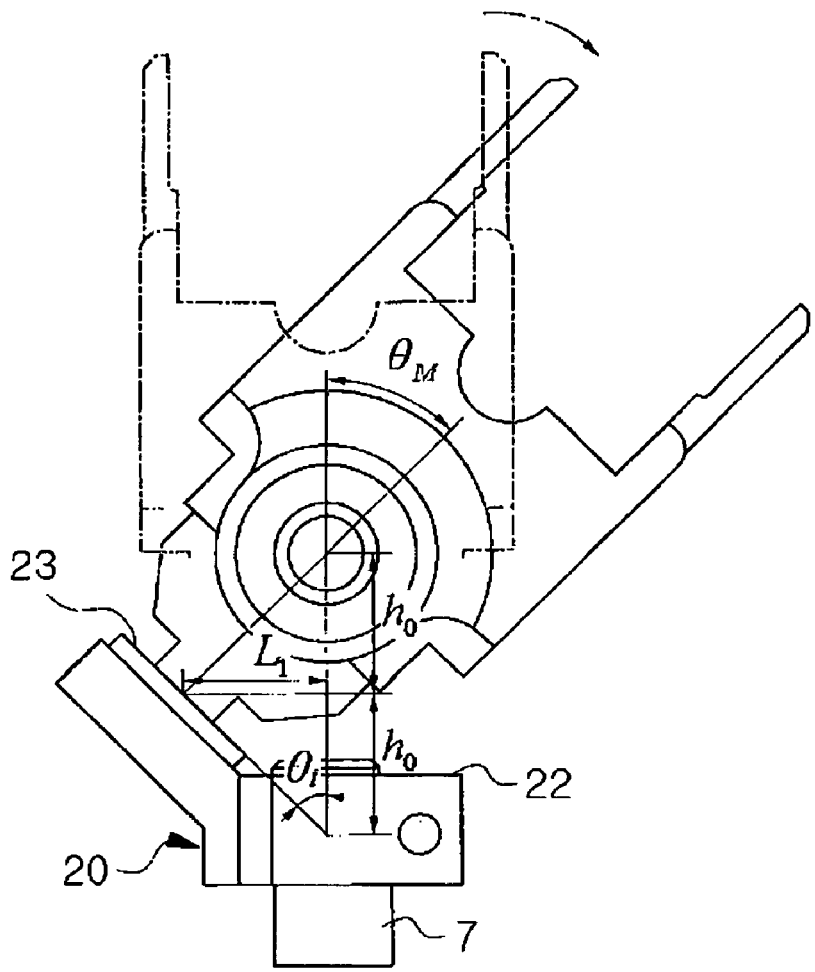
[Fig. 7]
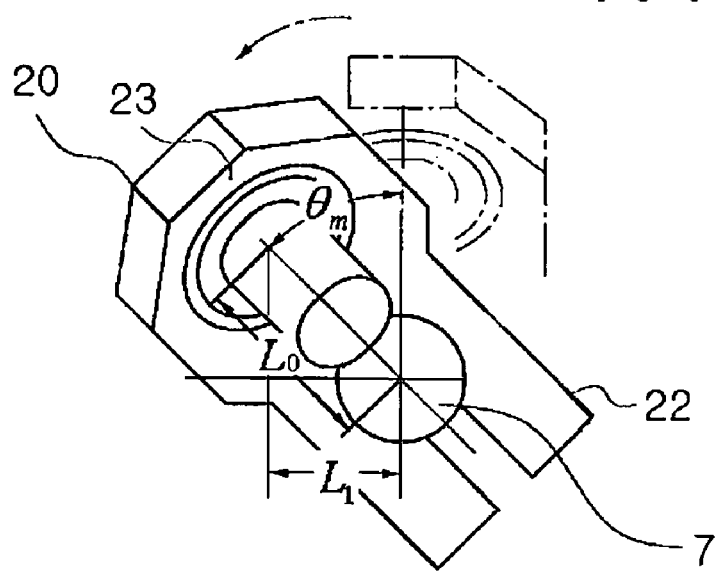
[Fig. 8]

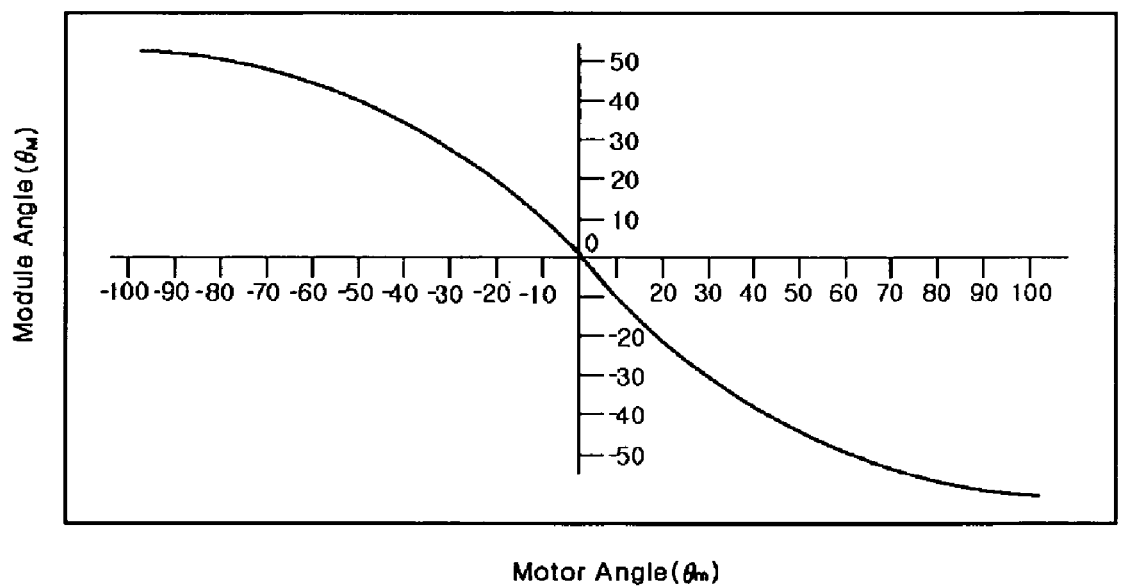
[Fig. 9]

ULTRASONIC PROBE FOR PRODUCING FOUR DIMENSIONAL IMAGE

TECHNICAL FIELD

The present invention relates to medical ultrasonic probes for producing a real-time 3 dimensional live action image (4 dimensional image), more particularly, to a medical ultrasonic probe which, not only has a simple structure and a long lifetime, but also is able to improve an image production characteristic in production of a real-time three dimensional live action image.

BACKGROUND ART

The medical ultrasonic probe, electrically connected to a system of a medical ultrasonic image diagnotor for producing an image by making a direct scanning of a human body intended to observe, is also called in general as a medical ultrasonic transducer or a medical ultrasonic probe.

In the medical ultrasonic probes which are essential elements for the medical ultrasonic image diagnotors, depending on the image the ultrasonic probe can produce, there are 2 dimensional image ultrasonic probes which can produce 2 dimensional sectional images, 3 dimensional image ultrasonic probes which can produce 3 dimensional images, and 4 dimensional image ultrasonic probes which can produce 3 dimensional real-time live action images which are in general defined as 4 dimensional images.

In the field of art the present invention is related thereto, there have been active researches and developments of 4 dimensional image ultrasonic probes which enable to make a real time observation of a live action image, such as motion of an unborn child, by a know method in which one dimensional array of acoustic elements each for making direct reception/transmission of an acoustic signal swing around a shaft of the one dimensional array, to obtain the 4 dimensional image.

As examples of known arts for producing the 4 dimensional image by the method in which the acoustic elements swing around the shaft of the one dimensional array of the acoustic elements, there are an ultrasonic probe for producing a real time three dimensional live action image (Korea Patent Registration No. 455606) in which the acoustic elements swing around the shaft of the acoustic element array by a power transmitted thereto from an upright motor through power transmission means, such as pulleys and wires, an image diagnosis sector probe (Korea Patent Registration No. 393354) in which the acoustic elements swing around the shaft of the acoustic element array by a power transmitted thereto from an upright motor through power transmission means, such as gears, and an European Patent (EP 1,208,800A2) in which the swing of a transducer is controlled by a belt that is connected between a motor shaft and a driving shaft of the transducer.

DISCLOSURE OF INVENTION

Technical Problem

However, the related art ultrasonic probes for producing a 4 dimensional image have a problem in that a structure for swinging acoustic elements around the shaft of the one dimensional array is complicate, and consequently, have many components, which impairs productivity, and leads to have a short lifetime.

Moreover, the related art ultrasonic probes for producing a 4 dimensional image have problems in that an image production characteristic, or function is poor due to a poor initial position control performance of the acoustic elements that swing.

Technical Solution

Accordingly, the present invention is directed to an ultrasonic probe for producing a 4 dimensional image, that substantially obviates one or more problems due to limitations and disadvantages of the related art.

An object of the present invention is to provide an ultrasonic probe for producing a 4 dimensional image, in which acoustic elements are made to swing around a shaft of one dimensional array of the acoustic elements by power transmitted through power transmission means, such as a link mechanism, for providing an ultrasonic probe for producing a 4 dimensional image, which has a simple structure and a small number of components to provide a good productivity and an improved lifetime.

Another object of the present invention is to provide an ultrasonic probe for producing a 4 dimensional image, which has a good initial position control performance to improve an image production performance.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, the ultrasonic probe for producing a four dimensional image includes power transmission means for transmission of power from an upright motor to a module having acoustic elements for swinging the module, the power transmission means includes a first link having a horizontal portion directly connected to a motor shaft, and a sloped portion projected upward from one side end of the horizontal portion at an angle in conformity with a locus of a swing action of the module, and a second link comprising a horizontal portion having an interlocking connected thereto and a pair of parallel portion projected upwardly from opposite ends of the horizontal portion, such that the second link is interlocked along the first link in a state of being interposed between the first link and the module, wherein the interlocking shaft is connected with an inclined portion of the first link by a shaft and the pair of parallel portions is mounting to a lower side of the module in a horizontal direction with a shaft.

The ultrasonic probe further includes a permanent magnet on the module and a first hall sensor and a second hall sensor mounted to predetermined points of the frame in correspondence to the permanent magnet according to a locus of a swing action of the module, wherein an initial position of the module is controlled by using an overlapped portion of signals detected by the first hall sensor and the second hall sensor.

Or alternatively, the ultrasonic probe further includes a permanent magnet on the first link and a first hall sensor and a second hall sensor mounted to predetermined points of the frame in correspondence to the permanent magnet according to a locus of a rotation of the first link, wherein an initial position of the module is controlled by using an overlapped portion of signals detected by the first hall sensor and the second hall sensor Advantageous Effects The ultrasonic probe for producing a four dimensional image of the present invention has advantages in that a structure thereof is simple to provide good productivity and a longer lifetime, and to permit to save a production cost, because the link mechanism which is power transmission means having simple and a small number of components transmits power from the motor to the module having acoustic elements to swing the module.

The construction of the power transmission means of a link mechanism for transmission of power from the motor to the module permits an accurate control of the swing action because almost no temporal error of driving and no positional error (gap) takes place, which is likely to take place between driving of a motor and the swing action of the module.

The good initial module position control performance improves a quality of the image, and prevents malfunction of the swing action of the module.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention, illustrate embodiment(s) of the invention and together with the description serve to explain the principle of the invention. In the drawings;

FIG. 1 illustrates a perspective view of an ultrasonic probe for producing a 4 dimensional image in accordance with a preferred embodiment of the present invention having a housing thereof removed therefrom;

FIG. 2 illustrates a perspective view of the ultrasonic probe for producing a 4 dimensional image in FIG. 1 having a frame thereof removed therefrom additionally for showing the probe in more detail;

FIG. 3 illustrates a section of key parts of the ultrasonic probe for producing a 4 dimensional image in FIG. 1 having the housing thereof removed therefrom;

FIG. 4 illustrates an exploded perspective view of the ultrasonic probe for producing a 4 dimensional image in FIG. 1 having the housing thereof removed therefrom;

FIG. 5 illustrates a diagram showing a hall sensor and permanent magnets mounted in the ultrasonic probe for producing a 4 dimensional image in FIG. 1;

FIG. 6 illustrates signal waveforms of the ultrasonic probe for producing a 4 dimensional image in FIG. 1 showing a timing of detection of positional signal of a hall sensor;

FIG. 7 illustrates a side view of the ultrasonic probe for producing a 4 dimensional image in FIG. 1 showing a motor rotation angle and a swing angle of a module, schematically;

FIG. 8 illustrates a plan view of the ultrasonic probe for producing a 4 dimensional image in FIG. 1 showing a motor rotation angle and a swing angle of a module, schematically; and FIG. 9 illustrates a graph showing a relation between a motor rotation angle and a swing angle of a module of the ultrasonic probe for producing a 4 dimensional image in FIG. 1.

BEST MODE FOR CARRYING OUT THE INVENTION

Reference will now be made in detail to the preferred embodiments of the present invention, examples of which are illustrated in the accompanying drawings. Wherever possible, the same reference numbers will be used throughout the drawings to refer to the same or like parts.

FIG. 1 illustrates a perspective view of an ultrasonic probe for producing a 4 dimensional image in accordance with a preferred embodiment of the present invention having a housing (not shown) thereof removed therefrom, and FIG. 2 illustrates a perspective view of the ultrasonic probe for producing a 4 dimensional image in FIG. 1 having a frame 3 thereof removed therefrom additionally for showing the probe in more detail, in which a module 2 has swung, slightly.

FIG. 3 illustrates a section of key parts of the ultrasonic probe for producing a 4 dimensional image in FIG. 1 having the housing (not shown) thereof removed therefrom, and FIG. 4 illustrates an exploded perspective view of the ultrasonic probe for producing a 4 dimensional image in FIG. 1 having the housing (not shown) thereof removed therefrom.

Referring to FIGS. 1 to 4, the ultrasonic probe for producing a 4 dimensional image includes a module 2 having acoustic elements for transmission/reception of an ultrasonic wave and a link mechanism 20 and 21 which is power transmission means mounted on the frame 3, a motor 4 under the frame 3 for generating power to swing the module 2, having an upright shaft (not shown) for reducing an entire size of the probe.

Units of the ultrasonic probe for producing a 4 dimensional image of the present invention will be described.

1. Motor

The motor 4, a power generating source, is mounted on an underside of the frame 3 with fastening means, such as flange 5 and bolts 26a, for generating power to swing the module 2 having acoustic elements which make direct reception/transmission of an ultrasonic wave around a shaft of one dimensional array of the acoustic elements.

The motor 4 is a step motor electrically connected to a motor driver (not shown) in a system (not shown) of a medial ultrasonic image diagnotor, for making regular/reverse direction rotation and stepping rotation in response to an electric signal from the motor driver, in which the module 2 makes stepping rotation according to stepping rotation of the motor shaft (not shown).

Over the motor 4, there is speed reduction means 6, such as an assembly of a planetary gear train, for speed reduction and transmission of the rotation of the motor shaft (not shown) to the module 2. Transmitting the rotation of the motor shaft (not shown) to the module 2 at a speed reduced according to a reduction ratio of the reduction means 6, to enable the module 2 to swing at smaller steps, the speed reduction means 6 can provide a good quality image owing to the smaller steps.

The speed reduction means 6 may not be employed depending on a stepping control performance of the motor driver (not shown) and the motor 4, and the speed reduction means is not limited to the assembly of the planetary gear train, but may be other speed reduction means as far as the means is substitutional.

Refer to the ultrasonic probe for producing a real time three dimensional live action image disclosed in Korea Patent Registration No. 455606 for details of the assembly of the planetary gear train.

The motor 4 and the reduction means 6 may be fabricated as one unit, or detachable so as to fasten with screws, and is not limited to only one type.

On the reduction means 6, there is a flange 5 fastened to the reduction means 6 with screws or the like for joining the motor 4 and the reduction means 6 to the frame 3. The flange 6 is also joined to the frame 3 at an underside thereof with screws or the like.

The joining method of the motor 4 and the reduction means 6 to the flange 5, and the joining method of the flange to the frame 3 are not limited to above screw joining, but other joining methods may be applied thereto as far as the methods are within a range of variation/modification or substitutional of above joining method.

2. Frame

Though the frame 3 has an oval section substantially, since it is adequate if the frame 3 has a shape in conformity with a locus of the swing of the module 2 like a shape of the module 2, the shape of the frame 3 is not necessarily limited to the oval shape.

The frame 3 includes a shaft hole 8 in a bottom for rotatable pass through of a rotation shaft 7 which is an output side of the reduction means 6, and upward projections 9 and 10 at opposite sides for mounting the module 2 on a shaft so as to swing around the shaft.

As another embodiment of the present invention, in a case no reduction means is employed, a motor shaft (not shown) of the motor 4 is rotatably passed through the shaft hole 8 in the bottom of the frame 3.

Of course, a profile of the frame 3 may be changed depending, not only on the shape of the module 2 and the locus of swing of the module 2, but also on a design of the housing (not shown).

3. Module

The module 2 of the ultrasonic probes for producing a four dimensional image of the embodiment includes a piezo electricity ceramic (not shown), a matching layer (not shown), a backing (not shown), a lens 2b, and so on housed in a module housing 2a, a link mechanism 20 and 21, which is a power transmission means and will be described later, mounted on a shaft on a lower side of the housing 2a in a horizontal direction, and opposite sides of the module housing 2a mounted on the frame 3 with shafts so as to be able to swing around the shafts.

It is adequate as far as the module 2 is mounted on the frame 3 with the shafts so as to be able to swing around the shafts by power from the motor 4. Mounting methods of the module 2 and the frame 3 with the shafts are not limited to a particular design.

The module housing 2a has downward projections 11 and 12 from opposite sides with shaft holes 13 and 14 formed therein with bearings 15 and 16 mounted therein respectively. There are shafts 17 and 18 are mounted on the bearings 15 and 16 respectively, for swinging the module 2.

At first, the piezo electricity ceramic (not shown), the matching layer (not shown), and the backing (not shown) are placed in the module housing 2a in a state the piezo electricity ceramic (not shown), the matching layer (not shown), and the backing (not shown) are bonded together. Then, a lens material is molded to form the lens 2b as one body with the module housing 2a.

A method for fabricating the module 2 is not limited to above method in which a lens material is molded to form the lens 2b as one body with the module housing 2a, but a method is viable in which the piezo electricity ceramic (not shown), the matching layer (not shown), and the backing (not shown) and the lens 2b are placed in the module housing 2a in a state the piezo electricity ceramic (not shown), the matching layer (not shown), and the backing (not shown) are bonded together and the lens 2b is formed. Thus, it is not necessary to limit the method for fabricating the module 2 to a particular method or system.

In general, elements of the module 2, i.e., the piezo electricity ceramic (not shown), the matching layer (not shown), and the backing (not shown), the lens 2b, electric lines 19, and so on are not limited to above in the field of the art, but removal of some of the elements, or substitution with other elements is still within a scope of the present invention as far as the module 2 is within a range that meets functions for converting an acoustic signal to an electric signal, and vice versa, and transmitting/receiving an ultrasonic signal.

It is adequate that the electric lines 19 are connected to the acoustic elements so that the piezo electricity ceramic (not shown) is driven by an electric signal to generate an acoustic signal, or meets a function of sensing the piezo electricity ceramic (not shown) driven by the acoustic signal. The electric lines 19 may be one selected from wire cable, flexible or hard type printed circuit board, flexible flat cable, and so on, or a combination of some of above, but are not limited, specifically.

The electric lines 19 are lead through an electric line opening 2c at a lower side of the module housing 2a, between the module housing 2a and the frame 3, and an electric line opening 3a at a lower side of the frame 3, and connected to an ultrasonic image diagnotor system (not shown).

4. Link Mechanism

The link mechanism, which is power transmission means of the ultrasonic probe for producing a four dimensional image includes a first link 20 directly connected to the rotation shaft 7, and a second link 21 between the first link 20 and the module housing 2a.

The first link 20 includes a horizontal portion 22 inserted on the rotation shaft 7, and a sloped portion 23 sloped upward from one side end of the horizontal portion 22 at a predetermined angle q having the second link 21 mounted thereon with a shaft so as to interlock the sloped portion 23 with the second link 21.

The horizontal portion 22 of the first link 20 has a shaft hole 51 for placing the rotation shaft 7 therein, a cut away portion 25 having a portion cut away therefrom for easy mounting of the rotation shaft to the shaft hole 51, and a bolt 26 for fastening the cut away portion 25 to make connection between the shaft hole 51 and the rotation shaft 7 rigid after the rotation shaft 7 is placed in the shaft hole 51.

It is not necessary to limit the rigid connection between the first link 20 and the rotation shaft 8 to the use of the bolt.

The sloped portion 23 of the first link 20 has a shaft hole 27 for mounting the second link 21 with a shaft to interlock the sloped portion 23 with the second link 21, and is sloped at 135° from the horizontal portion 22. However, the angle between the horizontal portion 22 and the sloped portion 23 is not limited to this, but may vary according to a size of the locus of the swing of the module 2.

The second link 21 includes a horizontal portion 29 for connection to an interlocking shaft 28 for mounting the first link 20 with the shaft, and one pair of parallel portions 30 and 31 projected upward from opposite sides of the horizontal portion 29 for mounting to the module housing 2a perpendicular to an underside of the module housing 2a with shafts.

The horizontal portion 29 of the second link 21 has a shat hole 27 for connection to the interlocking shaft 28, preferably with a bearing therein for rotation of the interlocking shaft 28, but of course not limited thereto.

The module housing 2a includes a downward projection 33 having a shaft hole 34, and each of the parallel portions 30 and 31 of the second link mechanism 21 has a shaft hole 35 or 36 with a bearing 37 or 38 therein, wherein the downward projection 33 and the parallel portions 30 and 31 are coupled with shafts 39 and 40 passed through the shaft holes 35 and 36 and placed in the shaft hole 34, with bearings 37 and 38 between the shaft holes 35 and 36 and shafts 39 and 40 respectively, but of course not limited thereto.

In the case no reduction means 6 is employed, the motor shaft (not shown) is placed in the shaft hole 51 in the horizontal portion 22 of the first link 20 in press fit.

Because a rotation power of the motor 4 is transmitted to the module 2 as it is without temporal and positional errors (a gap) through the plurality of links 20 and 21, which is power transmission means, the swing of the module 2 is controlled precisely.

That is, since rotation power transmission from the motor 4 to the module 2 is made directly by the links 20, and 21, preventing an error of a swing time period caused by slip between the pulley and the wire in the power transmission or an assembly error (a gap) between the pulley and the wire from taking place, the precise control of the module 2 can be made.

Particularly, as described before, in the present invention, the rotation power of the motor 4 can be transmitted to the module 2 precisely by using the links 20 and 21, and furthermore, the swing of the module 2 can be controlled more precisely as the links 20 and 21 are arranged in three dimension at predetermined angles from the rotation shaft of the motor 4, resulting to have acceleration/deceleration periods according to a locus of swing of the module 2.

That is, because the first link 20 sloped at a predetermined angle varies an angle of the rotation shaft of the motor 4, and the second link 21 connected to the first link 20 in a state sloped at a predetermined angle is mounted to the module 4 with a shaft, arranging the links 20 and 21 three dimensionally and making rotation directions of the first link 20 and the second link 21 opposite, between a rotation angle of the rotation shaft of the motor 4 and a swing angle of the module 2, there is not a linear function, but a unique function having acceleration/deceleration periods.

FIG. 7 illustrates a side view of the rotation shaft of the motor rotated at a predetermined angle $q_m$, and FIG. 8 illustrates a plan view of FIG. 7.

Referring to FIGS. 7 and 8, if it is assumed that the sloped portion of the first link 20 has a 45 of slope angle qi, $L_1=L_0 \sin q_m$, and $\tan q_m L_1/h_0$. Since the links rotate in opposite directions, between the swing angle $q_m$ of the module and the rotation angle $q_m$ of the rotation shaft of the motor 4, there is a relation of a trigonometric function of $q_M = -\tan^{-1}(L_0/h_0) * \sin q_m$.

FIG. 9 illustrates a graph showing above trigonometric function, wherefrom it can be noted that, between the swing angle $q_M$ of the module 2 and the rotation angle $q_m$ of the rotation shaft of the motor 4, there is a relation of a sin function established. That is, in view of a characteristic of the sin function, at a starting and an end of the swing locus, decelerations are made, and in the middle of the swing locus, an acceleration is made.

Accordingly, at the starting and end of the swing action of the module, the swing action is smooth and precise owing to the deceleration, enabling to control the swing action of the module more precisely.

Since the acceleration/deceleration periods of the module vary with the angle between the horizontal portion 22 and the sloped portion 23 of the first link 20, the acceleration/deceleration periods can be adjusted freely as the user desires by varying the angle between the horizontal portion 22 and the sloped portion 23.

5. Hall Sensor and Permanent Magnet

FIG. 5 illustrates a diagram showing hall sensors 41 and 42 and a permanent magnet 43 mounted in the ultrasonic probe for producing a four dimensional image in FIG. 1, and FIG. 6 illustrates signal waveforms of the ultrasonic probe for producing a four dimensional image in FIG. 1 showing a timing of detection of positional signal of the hall sensors 41 and 42, showing a waveform of a signal S sensed/detected when the permanent magnet 43 on the module 2 approaches to the one pair of the hall sensors 41 and 42 respectively mounted at the opposite upward projections 10 of the frame 3 following the swing of the module 2, wherein t denotes a time axis.

The permanent magnet 43 is mounted at a predetermined point of one side of the module housing 2a which is to swing, and the one pair of the hall sensors, i.e., the first hall sensor 41 and the second hall sensor 42 are mounted at sides of the frame 3, for an example, predetermined points of the upward projections 10, corresponding to the point where the permanent magnet 41 is mounted.

The hall sensors 41 and 42 are mounted at opposite sides of a centerline of the swing action of the module 2 close to the permanent magnet within a range in which the hall sensors 41 and 42 sense the permanent magnet wrongly, of course depending on a size of swing action of the module 2 and/or a signal detection performance of the hall sensors 41 and 42.

Referring to FIG. 3, between each of the upward projections 9 and 10 of the frame 3 and the module 2, there is a gap 44 for preventing the upward projections 9 and 10 of the frame 3 and the module 2 from being in contact (mechanical interference), thereby the swinging module 2 being not in contact or interfere with the upward projections 9 and 10 of the frame 3.

Referring to FIG. 6, an initial position of the module 2 is sensed by using an overlapped portion P of the signals sensed/detected by the first hall sensor 41 and the second hall sensor 42, for making a more accurate control of the initial position of the module 2 and preventing the module 2 from making a wrong swing action.

As an alternative, the permanent magnet 43 may be mounted to the first link 20 at a predetermined point, and the one pair of hall sensors, i.e., the first hall sensor 41 and the second hall sensor 42, may be mounted at predetermined points of sides of the frame 3 corresponding to the point where the permanent magnet 41 is mounted.

Other than above elements, though the ultrasonic probe also includes acoustic fluid (not shown) for transmission of an acoustic signal between the acoustic elements and the human body, a cover case (not shown) for enabling the swing action of the module 2 and sealing the acoustic fluid (not shown), the housing (not shown) inclusive of a handle case (not shown) serving as a hand grip, detailed description of which will be omitted as those are not only known, but also not required to be specific.

The ultrasonic probe for producing a four dimensional image of the present invention is electrically connected to a system (not shown) of a medical ultrasonic image diagnotor, so that the motor 4 makes a regular/reverse direction rotation and a stepping rotation in response to a control signal from a motor driver (not shown), for transmission of the power from the motor 4 to the link mechanism 20 and 21 and the module 2 through the rotation shaft 7 after a speed is reduced by the reduction means 6.

Eventually, the module 2 enables to obtain a four dimensional image (a real time three dimensional live action image) while the module 2 is swinging around the shaft of the one dimensional array of the acoustic elements.

Since the power is transmitted from the motor 4 to the module 2 by power transmission means having simple and small number of components, such as the first link 20 directly connected to the rotation shaft 7, and the second link 20 connected to the first link 20 with the interlocking shaft 28 and to the module housing 2a with a shaft, the ultrasonic probe for producing a four dimensional image of the present invention, not only has a good productivity and a long lifetime, but also saves a production cost.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

INDUSTRIAL APPLICABILITY

The ultrasonic probe for producing a four dimensional image of the present invention has a significantly high industrial applicability owing to the design of the swing action of the module made by a link mechanism of a power transmission means having simple and small number of components to have a simple structure, which provides good productivity and a long lifetime, and an accurate control of the swing action without malfunction of the module to improve a quality of the image produced.

The invention claimed is:

1. An ultrasonic probe for producing a four dimensional image, comprising power transmission means for transmission of power from an upright motor to a module having acoustic elements for swinging the module, the power transmission means including; a first link having a horizontal portion directly connected to a motor shaft, and a sloped portion projected upward from one side end of the horizontal portion at an angle in conformity with a locus of a swing action of the module, and a second link comprising a horizontal portion having an interlocking connected thereto and a pair of parallel portion projected upwardly from opposite ends of the horizontal portion, such that the second link is interlocked along the first link in a state of being interposed between the first link and the module, wherein the interlocking shaft is connected with an inclined portion of the first link by a shaft and the pair of parallel portions is mounting to a lower side of the module in a horizontal direction with a shaft.

2. The ultrasonic probe as claimed in claim 1, further comprising reduction means mounted on the motor for reducing a rotation speed of the motor shaft before transmission of rotation of the motor shaft to the first link, the reduction means having a rotation shaft which is an output shaft directly connected to the first link.

3. The ultrasonic probe as claimed in claim 2, wherein the first link includes; the horizontal portion directly connected to the rotation shaft, and the sloped portion projected upward from one side end of the horizontal portion at a predetermined angle.

4. The ultrasonic probe as claimed in claim 3, further comprising a permanent magnet on the module and a first hall sensor and a second hall sensor mounted to predetermined points of the frame in correspondence to the permanent magnet according to a locus of a swing action of the module, wherein an initial position of the module is controlled by using an overlapped portion of signals detected by the first hall sensor and the second hall sensor.

5. The ultrasonic probe as claimed in claim 3, further comprising a permanent magnet on the first link and a first hall sensor and a second hall sensor mounted to predetermined points of the frame in correspondence to the permanent magnet according to a locus of a rotation of the first link, wherein an initial position of the module is controlled by using an overlapped portion of signals detected by the first hall sensor and the second hall sensor.

6. The ultrasonic probe as claimed in claim 2, further comprising a permanent magnet on the module and a first hall sensor and a second hall sensor mounted to predetermined points of the frame in correspondence to the permanent magnet according to a locus of a swing action of the module, wherein an initial position of the module is controlled by using an overlapped portion of signals detected by the first hall sensor and the second hall sensor.

7. The ultrasonic probe as claimed in claim 2, further comprising a permanent magnet on the first link and a first hall sensor and a second hall sensor mounted to predetermined points of the frame in correspondence to the permanent magnet according to a locus of a rotation of the first link, wherein an initial position of the module is controlled by using an overlapped portion of signals detected by the first hall sensor and the second hall sensor.

8. The ultrasonic probe as claimed in claim 1, further comprising a permanent magnet on the module and a first hall sensor and a second hall sensor mounted to predetermined points of the frame in correspondence to the permanent magnet according to a locus of a swing action of the module, wherein an initial position of the module is controlled by using an overlapped portion of signals detected by the first hall sensor and the second hall sensor.

9. The ultrasonic probe as claimed in claim 1, further comprising a permanent magnet on the first link and a first hall sensor and a second hall sensor mounted to predetermined points of the frame in correspondence to the permanent magnet according to a locus of a rotation of the first link, wherein an initial position of the module is controlled by using an overlapped portion of signals detected by the first hall sensor and the second hall sensor.

* * * * *